United States Patent [19]

Stern

[11] Patent Number: 4,606,737

[45] Date of Patent: Aug. 19, 1986

[54] FLUOROCHEMICAL ALLOPHANATE COMPOSITIONS AND FIBROUS SUBSTRATES TREATED THEREWITH

[75] Inventor: Richard M. Stern, Woodbury, Minn.

[73] Assignee: Minnesota Mining and Manufacturing Company, Saint Paul, Minn.

[21] Appl. No.: 625,028

[22] Filed: Jun. 26, 1984

[51] Int. Cl.$^4$ .................. C07C 125/06; C10M 105/76
[52] U.S. Cl. ........................................ 8/115.6; 8/615; 252/8.75; 252/8.8; 252/182; 560/13; 560/24; 560/25; 560/27; 560/158
[58] Field of Search ................ 8/615, 115.6; 560/158, 560/24, 25, 27, 13; 252/8.75, 8.8

[56] References Cited

U.S. PATENT DOCUMENTS

| | | | |
|---|---|---|---|
| 3,329,661 | 7/1967 | Smith et al. | 523/414 |
| 3,398,182 | 8/1968 | Guenthner | 260/455 |
| 3,458,571 | 7/1969 | Tokoli | 564/96 |
| 3,462,296 | 8/1969 | Raynolds et al. | 117/161 |
| 3,574,791 | 4/1971 | Sherman et al. | 525/276 |
| 3,728,151 | 4/1973 | Sherman et al. | 117/138.8 |
| 3,896,251 | 7/1975 | Landucci | 428/290 |
| 3,916,053 | 10/1975 | Sherman et al. | 428/96 |
| 4,013,627 | 3/1977 | Temple | 526/245 |
| 4,024,178 | 5/1977 | Landucci | 560/25 |
| 4,029,585 | 6/1966 | Dettre et al. | 252/8.6 |
| 4,144,367 | 3/1979 | Landucci | 428/96 |
| 4,165,338 | 8/1979 | Katsushima et al. | 564/391 |
| 4,190,545 | 2/1980 | Marshall et al. | 252/8.75 |
| 4,215,205 | 7/1980 | Landucci | 525/331 |
| 4,264,484 | 4/1981 | Patel | 524/168 |
| 4,325,857 | 4/1982 | Champaneria et al. | 523/412 |
| 4,401,780 | 8/1983 | Steel | 524/225 |
| 4,426,476 | 1/1984 | Chang | 524/288 |
| 4,473,371 | 9/1984 | Schinzel et al. | 8/115.65 |
| 4,500,438 | 2/1985 | Kelly | 252/8.75 |
| 4,539,006 | 9/1985 | Langford | 252/8.75 |
| 4,540,497 | 9/1985 | Chang et al. | 252/8.8 |
| 4,560,487 | 12/1985 | Brinkley | 252/8.8 |
| 4,566,981 | 1/1986 | Howells | 252/8.8 |

FOREIGN PATENT DOCUMENTS 57-164181  10/1982  Japan .

OTHER PUBLICATIONS

Banks, R. E., Ed. "Organofluorine Chemicals and Their Industrial Applications", Ellis Horwood, Ltd., West Sussex, England 226–230 (1979).

*Primary Examiner*—A. Lionel Clingman
*Attorney, Agent, or Firm*—D. M. Sell; J. A. Smith; C. Truesdale

[57] ABSTRACT

Fluorochemical allophanates containing one or more monovalent fluoroaliphatic radicals having at least three fully fluorinated terminal carbon atoms and one or more allophanate moieties, the radicals and moieties bonded together by hetero atom-containing or organic linking groups are provided. These fluorochemical allophanates are useful in the form of aqueous dispersions or emulsions or organic solutions in the treatment of fibrous substrates, such as textile fibers, to impart oil and water repellency.

29 Claims, No Drawings

FLUOROCHEMICAL ALLOPHANATE COMPOSITIONS AND FIBROUS SUBSTRATES TREATED THEREWITH

TECHNICAL FIELD

This invention relates to the treatment of fibrous substrates, such as textile fibers, carpet, paper, and leather, with fluorochemicals to impart oil and water repellency, and to the resulting treated substrates. In another aspect, it relates to the treatment of carpet fiber with a finish comprising fluorochemicals to impart oil and water repellency and soil resistance to such fiber. In another aspect, it relates to fluoroaliphatic radical-containing compositions, solutions, dispersions, and emulsions, and their preparation, which are useful in such treatment.

BACKGROUND ART

In the industrial production of textile articles, such as carpet and apparel, and such other fibrous substrates as paper and leather, it is common to treat such substrates with fluorochemicals containing fluoroaliphatic radicals (often designated by the symbol "$R_f$") to impart oil and water repellency to the surface of such substrates. Fluorochemicals of this type and their application to fibrous substrates are described in various prior art publications, e.g., U.S. Pat. Nos. 3,329,661 (Smith et al), 3,398,182 (Guenthner et al), 3,458,571 (Tokoli), 3,574,791 (Sherman et al), 3,728,151 (Sherman et al), 3,916,053 (Sherman et al), 4,144,367 (Landucci), 3,896,251 (Landucci), 4,024,178 (Landucci), 4,165,338 (Katsushima et al), 4,190,545 (Marshall), 4,215,205 (Landucci), 4,013,627 (Temple), 4,264,484 (Patel), 4,426,476 (Chang), 4,029,585 (Dettre), 3,462,296 (Raynolds et al), 4,401,780 (Steel), 4,325,857 (Champaneria et al), Japanese Laid-open publication 57-164181, and Banks, R. E., Ed. "Organofluorine Chemical and their Industrial Applications", Ellis Horwood, Ltd., West Sussex, England 226–230 (1979).

Although some fluorochemicals are useful in many applications and many are commercial products, some are relatively expensive to prepare and apply, others are difficult to apply, and others are not durable or do not impart the required properties to the extent desired.

Conventionally, fluorochemical compositions are applied to fibrous substrates, e.g., textiles and textile fiber, as solutions in organic solvents or as aqueous emulsions, as described in the above cited references, e.g., U.S. Pat. Nos. 3,329,661 and 4,024,178.

It is an object of this invention to provide a fluorochemical allophanate and method for its preparation.

Another object of this invention is to provide fluorochemical allophanates, including anionic and cationic derivatives thereof, useful for treating porous substrates, such as carpet fibers and carpet, for imparting oil, water and soil resistance thereto.

A further object of this invention is to provide fluorochemical allophanates in the form of stable emulsions, microemulsions and dispersions useful for the treatment of porous substrates, such as fibers, paper, leather and the like to impart oil, water and soil resistance thereto.

A still further object of this invention is to provide blends of fluorochemical allophanates and fluorochemical poly(oxyalkylenes), which blends can be used in the form of aqueous dispersions, emulsions and microemulsions to treat fibrous substrates such as textile fibers, filaments, yarns, or finished fibrous articles, such as carpet, and other fibrous substrates such as paper and leather, to impart oil and water repellency and soil resistance thereto.

A still further object of this invention is to provide blends of fluorochemical allophanates and a composition selected from fluorochemical urethanes, fluorochemical polyacrylates, hydrocarbon polyacrylates, and combinations thereof, which blends can be used to treat fibrous substrates to impart oil and water repellency and soil resistance thereto.

A still further object of the present invention is to provide a process for preparing the compositions of the invention, called "fluorochemical allophanates" herein.

BRIEF DESCRIPTION

This invention provides, in one aspect, fluorochemical allophanates which have one or more monovalent fluoroaliphatic radicals ($R_f$) having at least three fully fluorinated terminal carbon atoms, one or more allophanates moieties

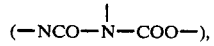

and can have organo amino or acid moieties, such as carboxylic, sulfonic, and phosphorus acid moieties, and salts formed from the compounds containing the organo amino or acid moieties, such radicals and allophanate moieties being linked or bonded together by first hetero atom-containing or organic linking groups, and where said fluorochemical allophanates are free of amino and acid moieties, two or more of said linked fluoroaliphatic radicals and allophanate moieties are linked or bonded together by polyvalent second hetero atom-containing or organic linking groups.

This invention also provides, in another aspect, blends of (a) the fluorochemical allophanate, and (b) normally liquid or low melting solid, water soluble or dispersible, fluoroaliphatic radical-containing poly(oxyalkylene).

The fluorochemical allophanate and the blends of (a) the fluorochemical allophanate and (b) the fluorochemical poly(oxyalkylene) are useful in the form of aqueous suspensions, emulsions, and microemulsions, and organic solutions in the treatment of fibrous substrates, such as textile fibers during manufature, and useful also in the treatment of finished or fabricated fibrous substrates such as carpets, paper and leather, to impart oil and water repellency thereto.

This invention further provides blends of (a) the fluorochemical allophanate and (c) fluorochemical urethanes, fluorochemical polyacrylates, hydrocarbon polyacrylates, and combinations thereof, which blends can be used in the form of aqueous dispersions, emulsions and microemulsions to treat fibrous substrates such as textile fibers, filaments, yarns, or finished fibrous articles, such as carpet, and other fibrous substrates such as paper and leather, to impart oil and water repellency and soil resistance thereto.

This invention also provides a process for producing compositions of the present invention, called "fluorochemical allophanates" herein by (a) reacting alcohol containing a fluoroaliphatic radical having at least three fully fluorinated terminal carbon atoms with an organic diisocyanate under urethane forming conditions to form fluorochemical isocyanate-containing urethane adduct, (b) heating the adduct under allophanate forming reaction conditions to form a fluorochemical isocyanate-containing allophanate intermediate, and (c) reacting said intermediate (1) with a reactant selected from polyol or polyamine under urethane or urea forming reaction conditions to produce fluorochemical allophanate, or (2) with a reactant selected from a polyamine, an alcohol containing an acid moiety, and an alcohol containing an amine moiety under urethane or urea forming reaction conditions to produce an amino- or acid-containing fluorochemical allophanate, and then, neutralizing said amino- or acid-containing fluorochemical allophanate to form fluorochemical allophanate salts, or (3) with a reactant selected from a polyamine or an amino alcohol under urethane or urea forming reaction conditions to produce an amino-containing fluorochemical allophanate, and then, alkylating said amino-containing fluorochemical allophanate to form fluorochemical allophanate salts.

DETAILED DESCRIPTION

A class of the fluorochemical allophanates of this invention can be represented by the general formula I

where $R^1$ is an organic radical, preferably aliphatic; $R^2$ is selected from H or $CONH-A-NHCOOQR^3$; $R^3$ is a terminal monovalent organic radical which can contain a fluoroaliphatic radical ($R_f$); A is an organic linking group which can contain an $R_f$ radical; Q is a linking group; X is O, S or $NR^4$, where $R^4$ is H or lower alkyl having 1 to 4 carbon atoms; $R^1$ and $R^3$ can contain substituents such as hydroxyl, chlorine, and amino or acid groups, and at least one $R^3$ or A contains an $R_f$ group; a is a number from 0 to 1; m and n are independently numbers from 0 to 10, the sum of m and n is 1 to 10, and each of the moieties denoted by subscripts m and n, when both are present, are randomly distributed in a chain within the brackets, [ ]; p is a number from 2 to 6, except that when $R^1$, $R^3$, or both $R^1$ and $R^3$ contain an amino or acid group, then p is a number from 1 to 6. The class also includes salts of the fluorochemical allophanates containing the amino or acid groups.

Another class of the fluorochemical allophanates is represented by formula II

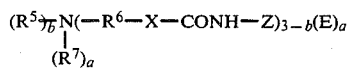

where Z is

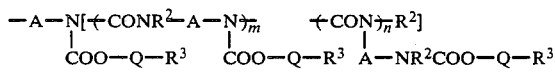

in which $R^2$, $R^3$, A, Q, X, a, m and n are as defined for formula I; $R^5$ is a monovalent radical selected from H, alkyl, aryl, cycloaliphatic groups and combinations thereof, which groups can contain $R_f-Q-$ radicals; $R^6$ is a divalent organic radical, preferably alkylene; $R^7$ is selected from H, lower alkyl groups having 1 to 4 carbon atoms, and aralkyl groups having 7 to 13 carbon atoms; E is an anion derived from a protonic acid or an alkylating agent selected, for example, from alkyl chlorides, bromides or iodides, dimethyl sulfate, diethyl sulfate, formic acid, acetic acid, glycolic acid, and citric acid; and b is a number from 0 to 2.

A further class of the fluorochemical allophanates is represented by general formula III

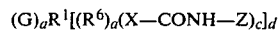

where $R^1$, $R^6$, X, Z, and a are as defined for formulas I and II; G is an anionic group selected from $COOM_{1/v}$, $SO_3M_{1/v}$, $PO(OM_{1/v})_2$, $OSO_3M_{1/v}$, and $OPO(OM_{1/v})_2$, where M is hydrogen or a cationic moiety such as an alkali metal, e.g., Na and K, or amino salt group, e.g., $N(C_2H_5)_3H$, or

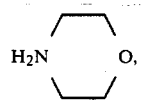

v is valence of M; c is a number from 1 to 2; and d is a number from 1 to 6, except when a is 0, then d is a number from 2 to 6.

In each of the above fluorochemicals, where there are a plurality of $R_f$, Q, A, $R^1$ through $R^7$ and X groups or moieties, each can be the same or different, e.g., in the case of two $R_f$ groups, one $R_f$ can be $C_8F_{17}-$ and the other can be $C_7F_{15}-$. Also, the allophanates of formulas I–III represent individual compounds or represent mixtures of such compounds, for example, as they are obtained as products from reactions used in their preparation. In addition, small amounts of by-products of such reactions, with and without fluoroaliphatic groups, and not represented by any of the formulas I–III, e.g. isocyanurates, di- or oligourethanes, can also be present in the mixtures or reaction products because of the reaction conditions involved in their preparation. Such presence of such small amounts of by-products, generally less than about 20 weight percent, does not detract from the usefulness of the fluorochemical allophanate mixtures or products of this invention and may be beneficial in the treatment of fibrous materials.

The fluoroaliphatic radical, $R_f$, referred to above, is a fluorinated, stable, inert, non-polar, preferably saturated, monovalent moiety which is both oleophobic and hydrophobic. It can be straight chain, branched chain, or, if sufficiently large, cyclic, or combinations thereof, such as alkylcycloaliphatic radicals. The skeletal chain in the fluoroaliphatic radical can include catenary oxygen, hexavalent sulfur, and/or trivalent nitrogen hetero atoms bonded only to carbon atoms, such hetero atoms providing stable linkages between fluorocarbon portions of $R_f$ and not interfering with the inert character of the $R_f$ radical. While $R_f$ can have a large number of carbon atoms, compounds where $R_f$ is not more than 20 carbon atoms will be adequate and preferred since large radicals usually represent a less efficient utilization of fluorine than is possible with smaller $R_f$ radicals. Generally $R_f$ will have 3 to 20 carbon atoms, preferably 6 to about 12, and will contain 40 to 78 weight percent, preferably 50 to 78 weight percent, fluorine. The terminal portion of the $R_f$ group has at least three fully fluorinated carbon atoms, e.g., $CF_3CF_2CF_2-$ and the preferred compounds are those in which the $R_f$ group is fully or substantially completely fluorinated, as in the case where $R_f$ is perfluoroalkyl, $C_nF_{2n+1}$.

The function of the linking group Q in the above formulas is to bond the $R^3$-radical, as in formula I, directly to the ether oxygen atoms in allophanate moieties or to bond polyvalent organic radicals as in formula III. Each Q can comprise a hetero atom-containing group or an organic group or a combination of such groups, examples of which are polyvalent aliphatic, e.g., $-CH_2-$, $-CH_2CH_2-$, and $-CH_2CH(CH_2-)_2$, polyvalent aromatic, oxy, thio, carbonyl, sulfone, sulfoxy, $-N(CH_3)-$, sulfonamido, carbonamido, sulfonamidoalkylene, e.g., $-SO_2NR^4(CH_2\!\!-\!\!)_e$, where e is 1 to 6, carbonamidoalkylene, carbonyloxy, urethane, e.g., $-CH_2CH_2OCONH-$, and urylene, e.g., $-NHCONH-$. The linkage Q for a specific fluorochemical allophanate useful in this invention will be dictated by the ease of preparation of such a compound and the availability of necessary precursors thereof. However, the Q group is preferably free of active (or isocyanate-reactive) hydrogen atoms, i.e., hydrogen atoms of groups such as mercapto, amino, and aliphatic hydroxyl groups that can react readily with isocyanate groups under urethane bond-forming conditions, e.g., 20°–100° C.

The polyvalent organic linking groups A in formula I, II and III above illustratively are alkylene groups, such as ethylene, isobutylene, hexylene, and methylenedicyclohexylene, having 2 to about 20 carbon atoms, arylene groups, such as tolylene, aralkylene groups, such as $-CH_2C_6H_4CH_2-$ and $-C_6H_4CH_2C_6H_4-$, having up to 20 carbon atoms, and various combinations of these groups. Such groups can also include from 1 to 10 $R_f$ groups, from 1 to 10 allophanate moieties and other hetero atom containing moieties, such as $-O-$, $-S-$, and $-N-$, e.g., $-(C_2H_4O)_zC_2H_4-$, where z is 1 to about 5. However, A is preferably free of groups with active hydrogen atoms.

The A group can be a residue of an organic diisocyanate from which the allophanate, urethane, urylene and other isocyanate-derived moieties arise, that is, A can be the divalent radical obtained by removal of the isocyanate groups from an organic diisocyanate. Suitable diisocyanate precursors may be simple, e.g., hexamethylene diisocyanate, xylylene diisocyanate, tolylene-2,4-diisocyanate, methylene bis(4-phenyleneisocyanate), and mixtures thereof, or complex, as formed by the reaction of a simple diisocyanate with an organic diol or polyol in appropriate proportions to yield an isocyanate-terminated polyurethane. Other polyisocyanates can also be used as starting materials. Some of these are described, for example, in U.S. Pat. No. 4,174,433. Representative A groups include $-CH_2C_6H_4CH_2C_6H_4CH_2-$, $-C_6H_{10}CH_2C_6H_{10}-$, $-(CH_2)_6-$, $-C_6H_4CH_2C_6H_4-$, $C_8F_{17}SO_2N\!\!-\!\!(C_2H_4OCONHC_6H_3(CH_3)\!\!-\!\!)_2$, $C_8F_{17}SO_2N(C_2H_5)C_2H_4OCONHC_6H_{12}N(CONHC_6H_{12}\!\!-\!\!)_2$, and $-(CH_2)_6[NHCOO(CH_2)_4OCONH(CH_2)_6\!\!-\!\!]_2$.

Generally, the fluorochemical allophanates of this invention will contain about 20 to 70 weight percent, preferably about 25 to 50 weight percent, of carbon-bonded fluorine. If the fluorine content is less than about 20 weight percent, impractically large amount of the fluorochemical allophanate compounds will generally be required, while fluorine contents greater than about 70 weight percent are unnecessary to achieve the desired surface properties in treating fibrous substrates and thus represent an uneconomical use of fluorine.

The fluorochemical allophanates of this invention can be prepared by the reaction of isocyanate group-containing compounds and urethanes at elevated temperatures, i.e., 60° C. or higher; and also by the reaction of alcohols with isocyanate dimers. (See Bruins, P. F., Ed., "Polyurethane Technology", Interscience Publishers, New York, N.Y., 21, 22, 42 (1969), for a general outline of these reactions.)

Compositions of the present invention, called "fluorochemical allophanates" herein, can be produced by (a) reacting alcohol containing a fluoroaliphatic radical having at least three fully fluorinated terminal carbon atoms with an organic diisocyanate under urethane forming conditions to form fluorochemical isocyanate-containing urethane adduct, (b) heating the adduct under allophnante forming reaction conditions to form a fluorochemical isocyanate-containing allophanate intermediate, and (c) reacting said intermediate (1) with a reactant selected from polyol or polyamine under urethane or urea forming reaction conditions to produce fluorochemical allophanate, or (2) with a reactant selected from a polyamine, an alcohol containing an acid moiety, and an alcohol containing an amine moiety under urethane or urea forming reaction conditions to produce an amino- or acid-containing fluorochemical allophanate, and then, neutralizing said amino- or acid-containing fluorochemical allophanate to form fluorochemical allophanate salts, or (3) with a reactant selected from a polyamine or an amino alcohol under urethane or urea forming reaction conditions to produce an amino-containing fluorochemical allophanate, and then, alkylating said amino-containing fluorochemical allophanate to form fluorochemical allophanate salts.

Representative reaction schemes for the preparation of fluorochemical allophanates of this invention are outlined below. In these schemes, a portion of the $R_f$—Q—OH reactant can be replaced by R—Q—OH where R is an organic radical as defined for $R^3$, preferably an alkyl radical.

In these schemes

Z′ is

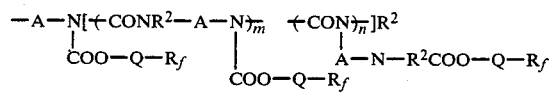

Z″ is 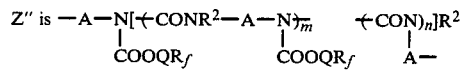

SCHEME 1

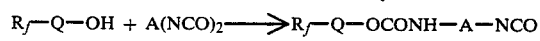

(step a)

-continued

SCHEME 1

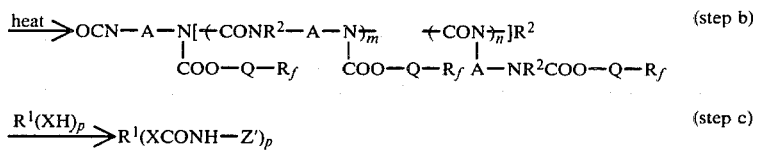   (step b)

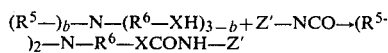 R¹(XCONH—Z')ₚ   (step c)

SCHEME 2

$(R^5\text{—})_b\text{—N—}(R^6\text{—XH})_{3-b} + Z'\text{—NCO} \rightarrow (R^5\text{—})_2\text{—N—}R^6\text{—XCONH—Z'}$ where b=2

The product of Scheme 2 can be reacted with an acid or alkylating agent to form a salt of the product.

SCHEME 3

$(HOOC\text{—})_a R^1(\text{—XH})_c + 2Z'\text{—NCO} \rightarrow HOOC\text{—}R^1(\text{—X—CONH—Z'})_2$ where a=1, c=2

SCHEME 4

$A(NCO)_2 + R^1(XH)_p + Z'\text{—NCO} + (HOOC\text{—})_a R^1(\text{—XH})_c \rightarrow HOOC\text{—}R^1[XCONH\text{—}A\text{—}NHCOX\text{—}R^1(\text{—XCONH—Z'})_2]_2$ where a=1, c=2, p=3

The products of Schemes 3 and 4 can be reacted with an amine or other base to form a salt of the respective products.

SCHEME 5

R_fQOH + A(NCO)₂ →

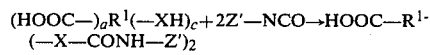

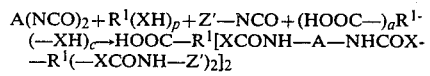

R¹[(XCONH)_{n+1}Z'']_p where m=1 or 2, n=1 or 2, p=2 or 3

SCHEME 6

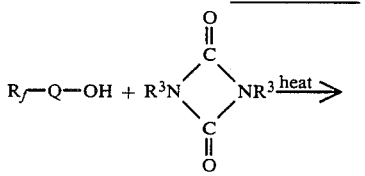

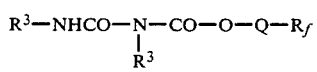

SCHEME 7

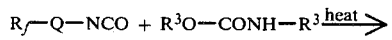

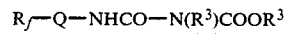

SCHEME 8

R_f—Q—NCO +

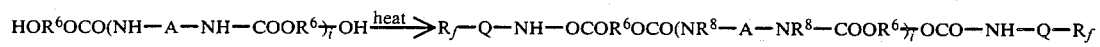

where R⁸=H or CONHQR_f, i=2 to 100.

Representative R_f intermediates for the preparation of the fluorochemical compositions of this invention include C₈F₁₇SO₂N(C₂H₅)C₂H₄OH, C₈F₁₇C₂H₄OH, C₇F₁₅CH₂OH, C₇F₁₅CON(C₂H₅)C₂H₄OH, C₈F₁₇C₂H₄SC₂H₄OH, (CF₃)₂CF(CF₂)₈C₂H₄OH, (CF₃)₂CFOC₂F₄C₂H₄OH, C₈F₁₇C₂H₄SO₂N(CH₃)C₄H₈OH, C₈F₁₇SO₂N(CH₃)C₃H₆NH₂,

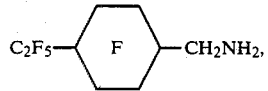

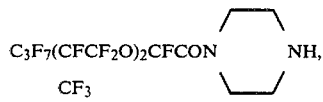

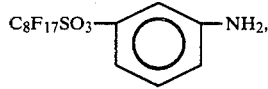

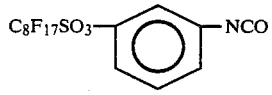

C₈F₁₇C₆H₄NH₂, C₈F₁₇C₆H₄NCO, C₇F₁₅CH₂NCO, C₈F₁₇C₂H₄SH, and C₇F₁₅CON(CH₃)C₂H₄SH.

Representative organic isocyanates include tolylene-2,4-diisocyanate, hexamethylene diisocyanate, methylenebis(4-phenyleneisocyanate), methylenebis(4-cyclohexyleneisocyanate), xylylene diisocyanate, 1-methoxy-2,4-phenylene diisocyanate, p-(1-isocyanatoethyl)phenyl isocyanate, phenyl isocyanate, m-tolyl isocyanate, 2,5-dichlorophenyl isocyanate, hexyl isocyanate, N,N',N''-tris(isocyanatohexyl)biuret, and isophorone diisocyanate, and mixtures thereof.

Representative isocyanate-reactive alcohol, mercapto, and amine reagents include ethylene glycol, 1,3-propanediol, 1,4-butanediol, glycerine, 1,1,1-trimethylolpropane, 1,3-dihydroxy-2-propane, 3-mercapto-1,2-propanediol, 2-aminoethanol, 3-amino-1-propanol, 1,4-diaminobutane, 1,6-diaminohexane, N(3-aminopropyl)diethanolamine, 3-amino-1,2-propanediol, triethylenetetramine, 2-dimethylaminoethanol, 2-diethylaminoethanol, 2-diisopropylaminoethanol, N-methyldiethanolamine, triethanolamine, 1-methyl-3-pyrrolidinol, 2(2-hydroxyethyl)pyridine, N(2-hydroxyethyl)morpholine, 1,4-bis(2-hydroxypropyl)piperazine, 1,1-dimethyl-4-dimethylamino-n-butanol, N(2-hydroxyethyl)pyrrolidine, 1-methyl-3-piperidinol, N(2-hydroxyethyl)-N-methylaniline, 2-dimethylaminoethanethiol, N,N-bis(2-mercaptoethyl)methylamine, 4-diethylamino-1-methyl-n-butanol, 1-dimethylamino-2-propanol, 3-dimethylamino-1-propanol, 3-dimethylamino-2-hydroxy-n-propanol, N,N-dimethyl-1,3-propanediamine, N(2-aminoethyl)-morpholine, 4(2-aminoethyl)-pyridine, and tris(2-aminoethyl)-amine, ethanol, octanol, octadecanol, 1-chloro-2,3-propanediol, hexylamine, dibutylamine, dodecylmercaptan, pentaerythritol, dipentaerythritol, sorbitol and mixtures thereof.

Representative hydroxy, mercapto and amino-group containing acids include 2,2-bis(hydroxymethyl)propionic acid, glycolic acid, 3-hydroxypropionic acid, glycine, 4-aminobutyric acid, mercaptoacetic acid, citric acid, malic acid, 3-aminopropane sulfonic acid, 4-hydroxybenzene sulfonic acid, 1,3-dihydroxybenzene sulfonic acid, and mixtures thereof.

Quaternizing alkylating agents and acids useful in this invention include methyl iodide, methyl bromide, allyl chloride, benzyl chloride, diethyl sulfate, dimethyl sulfate, bis(trifluoromethyl)sulfate, epichlorohydrin, hydrochloric acid, acetic acid, formic acid, and glycolic acid.

The fluoroaliphatic radical-containing poly(oxyalkylenes), called fluorochemical oxyalkylenes for brevity, used as component (b) in the fluorochemical blends of this invention are normally liquid or low melting solids. They contain one or more $R_f$ groups (as defined above), and one or more poly(oxyalkylene) moieties bonded together by hetero atom-containing or organic linking groups, or combinations of such groups.

A class of fluorochemical oxyalkylene used in this invention are fluoroaliphatic polymers (or oligomers, the term polymer hereinafter including oligomer unless otherwise indicated) represented by the general formulas:

   IV and

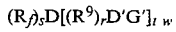   V where
$R_f$ is a fluoroaliphatic radical like that described above,
D is a linkage through which $R_f$ and $(R^9)_r$ moieties are covalently bonded together,
$(R^9)_r$ is a poly(oxyalkylene) moiety, $R^9$ being an oxyalkylene group with 2 to 4 carbon atoms and r is an integer (where the above formulas are those of individual compounds) or a number (where the above formulas are those of mixtures) at least 5, generally 10 to 75 and can be as high as 100 or higher,
G is a hydrogen atom or a monovalent terminal organic radical,
G' is G or a valence bond, with the proviso that at least one G' is a valence bond connecting a G-bonded $R^9$ radical to another D,
D' is a linkage through which G, or G', and $R^9$ are covalently bonded together,
s is an integer or number of at least 1 and can be as high as 25 or higher,
t is an integr or number of at least 1, and can be as high as 60 or higher, and
w is an integer or number greater than 1, and can be as high as 30 or higher.

In formulas IV and V, where there are a plurality of $R_f$ radicals, they are either the same or different. This also applies to a plurality of D, D', $R^9$, G, G', and, in formula V, a plurality of r, s, and t.

Generally, the oxyalkylene polymers will contain about 5 to 40 weight percent, preferably about 10 to 30 weight percent, of carbon-bonded fluorine. If the fluorine content is less than about 10 weight percent, impractically large amounts of the polymer will generally be required, while fluorine contents greater than about 35 weight percent result in polymers which have too low a solubility to be efficient.

In the poly(oxyalkylene) radical, $(R^9)_r$, $R^9$ is an oxyalkylene group having 2 to 4 carbon atoms, such as $-OCH_2CH_2-$, $-OCH_2CH_2CH_2-$, $-OCH(CH_3)CH_2-$, and $-OCH(CH_3)CH(CH_3)-$, the oxyalkylene units in said poly(oxyalkylene) being the same, as in poly(oxypropylene), or present as a mixture, as in a heteric straight or branched chain or randomly distributed oxyethylene and oxypropylene units or as in a straight or branched chain of blocks of oxyethylene units and blocks of oxypropylene units. The poly(oxyalkylene) chain can be interrupted by or include one or more catenary linkages. Where said catenary linkages have three or more valences, they provide a means for obtaining a branched chain or oxyalkylene units. The poly(oxyalkylene) radicals in the polymers can be the same or different, and they can be pendant. The molecular weight of the poly(oxyalkylene) radical can be as low as 200 but preferably is about 500 to 5,000.

The function of the linkages D and D' is to covalently bond the fluoroaliphatic radicals, $R_f$, the poly(oxyalkylene) moieties, $(R^9)_r$ and radicals G and G' together in the oligomer. D and D' can be a valence bond, for example where a carbon atom of a fluoroaliphatic radical is bonded or linked directly to a carbon atom of the poly(oxyalkylene) moiety. D and D' each can also comprise one of more linking groups such as polyvalent aliphatic and polyvalent aromatic, oxy, thio, carbonyl, sulfone, sulfoxy, phosphoxy, amine, and combinations thereof, such as oxyalkylene, iminoalkylene, iminoarylene, sulfoamido, carbonamido, sulfoamidoalkylene, carbonamidoalkylene, urethane, urea, and ester. The linkages D and D' for a specific oxyalkylene polymer will be dictated by the ease of preparation of such a polymer and the availability of necessary precursors thereof.

From the above description of D and D', it is apparent that these linkages can have a wide variety of structures, and in fact where either is a valence bond, it doesn't even exist as a structure. However large D and D' are, the fluorine content (the locus of which is $R_f$) is in the aforementioned limits set forth in the above description, and in general the sum of D and D' contents of the polymer is preferably less than 10 weight percent of the polymer.

The monovalent terminal organic radical, G, is one which is covalently bonded through D' to the poly(oxyalkylene) radical. Though the nature of G can vary, it preferably is such that it compliments the poly(oxyalkylene) moiety in maintaining or establishing the desired solubility of the oxyalkylene. The radical G can be a hydrogen atom, acyl, such as $C_6H_5C(O)-$, alkyl, preferably lower alkyl, such as methyl, hydroxyethyl, hydroxypropyl, mercaptoethyl and aminoethyl, or aryl, such as phenyl, chlorophenyl, methoxyphenyl, nonylphenyl, hydroxyphenyl, and aminophenyl. Generally, D'G will be less than 50 weight percent of the $(R^9)_rD'G$ moiety.

The fluoroaliphatic radical-containing poly(oxyalkylene) used in this invention can be prepared by a variety of known methods, such as by condensation, free radical, or ionic homopolymerization or copolymerization using solution, suspension, or bulk polymerization techniques, e.g., see "Preparative Methods of Polymer Chemistry", Sorenson and Campbell, 2nd ed., Interscience Publishers, (1968). Classes of representative poly(oxyalkylenes) useful in this invention include polyesters, polyurethanes, polyepoxides, polyamides, and vinyl polymers such as polyacrylates and substitute polystyrenes.

The polyacrylates are a particularly useful class of poly(oxyalkylenes) and they can be prepared, for example, by free radical initiated copolymerization of a fluoroaliphatic radical-containing acrylate with a poly(oxyalkylene)acrylate, e.g., monoacrylate or diacrylate or mixtures thereof. As an example, a fluoroaliphatic acrylate, $R_f-R''-O_2C-CH=CH_2$ (where R'' is, for example, sulfonamidoalkylene, carbonamidoalkylene, or alkylene), e.g., $C_8F_{17}SO_2N(C_4H_9)CH_2C-H_2O_2CCH=CH_2$, can be copolymerized with a poly(oxyalkylene)monoacrylate, $CH_2=CHC(O)(R^9)_rOCH_3$, to produce a polyacrylate oxyalkylenes.

Further description of fluorochemical oxyalkylenes useful in this invention will be omitted in the interest of brevity since such compounds and their preparation are known, and are described in U.S. Pat. No. 3,787,351 and U.S. Pat. No. 4,289,892, both of which are incorporated herein by reference.

The relative amounts of component (a), the fluorochemical allophanates, and component (b), the fluorochemical poly(oxyalkylene), in the fluorochemical blend used in this invention to treat porous, fibrous substrates can vary over a broad range and will be selected to provide the desired balance of surface properties on the treated fiber of the finished article. Generally, component (a) will be the major amount of the blend and component (b) will be the minor amount. The particular amount depends on the particular composition of the textile fiber or article to be treated and the particular chemical composition of (a) and (b), as well as the application procedures used.

Generally, the relative amounts of components (a) and (b) fall within the following ranges:

| | Amount of fluorochemical solids in blend (wt. %) | | |
|---|---|---|---|
| Component | General Broad Range | Preferred Broad Range | Most Preferred Range |
| (a) | 40 to 99 | 60 to 99 | 65 to 95 |
| (b) | 1 to 60 | 1 to 40 | 5 to 35 |

The fluorochemical allophanates of this invention, and blends thereof with fluorochemical poly(oxyalkylenes) can be utilized as solutions in organic solvents or as aqueous emulsions or dispersions. Aqueous emulsions and microemulsions are particularly useful forms for the fluorochemical allophanates and the blends thereof with poly(oxyalkylenes) of this invention because of the ease of formation and stability of these emulsions, especially when a salt forming moiety is present in the fluorochemical allophanate compositions.

In the preparation of these aqueous emulsions, it is generally beneficial in ease of formation and particularly in emulsion stability to include a nonionic surfactant, thus the blends of this invention comprising (a) the fluorochemical allophanate and (b) fluorochemical poly(oxyalkylenes) yield emulsion and microemulsions having excellent properties. Also these blends generally yield improved oil and water repellency when applied to porous substrates, e.g., carpet fibers and carpets.

Hydrocarbon nonionic surfactants are also beneficial in forming stable emulsions and microemulsions. These can be used in place of the fluorochemical nonionic surfactants, i.e., the fluorochemical poly(oxyalkylenes) or in addition to them as a co-surfactant. Hydrocarbon and fluorochemical anionic and cationic surfactants may also be beneficial as co-surfactants with the hydrocarbon and fluorochemical nonionic surfactants.

Representative hydrocarbon surfactants and co-surfactants useful in this invention include the following commercial poly(oxyalkylene) compounds: poly(oxyethylene)sorbitan monooleate, e.g., "Tween" 80; alkylaryl polyethylene glycol ether, e.g., "Surfonic" N-120; ethoxylated lauryl alcohol, e.g., "Siponic" L-16; octylphenoxy polyethoxy ethanol, e.g., "Triton" X-102; polyethylene glycol ether of primary alcohol, e.g., "Tergitol" 15-S-30; polyethylene glycol ether of sec. alcohol, e.g., "Tergitol" 15-S-15; poly(oxyethylene)-cetyl ether, e.g., "Brij" 58; and octylphenoxypoly(oxyethylene)ethanol, e.g., "Igepal" CA 720.

Each of these surfactants and co-surfactants has a hydrophile-lipophile balance value in the range of about 12 to 18. Those hydrocarbon poly(oxyalkylenes) with higher or lower values were found not to be as useful in promoting emulsion stability and quality, but may be useful in surfactant blends.

Additional hydrocarbon surfactants useful in this invention include: sodium lauryl sulfate, e.g. "Dupanol" QC and polyethoxylated quaternary ammonium salts, e.g. "Ethoquad" 18/25.

The fluorochemical allophanates of this invention may also be used in combination with other fluorochemical compounds, e.g., fluorochemical urethane, and with polymers, e.g., fluorochemical polyacrylates and hydrocarbon polyacrylates.

Substrates which can be treated in accordance with this invention are textile fibers (or filaments), and finished or fabricated fibrous articles such as textile products, paper, paperboard, leather, and the like. The fluorochemical allophanates of this invention are also useful as coatings for shaped articles to provide decorative or protective surfaces on the articles.

The textile products which may be treated with the fluorochemical allophanates of this invention include those made from natural fibers, such as cotton and wool and those made from synthetic organic fibers, such as nylon, polyolefin, acetate, rayon, acrylic, and polyester fibers. Especially good results are obtained on nylon and polyester fibers. The fibers or filaments as such or in an aggregated form, e.g., yarn, tow, web, or roving, or the fabricated textile, e.g., articles such as carpet and woven fabrics, can be treated with the fluorochemical allophanate or blends thereof with poly(oxyalkylenes). The treatment can be carried out by applying the fluorochemical allophanate composition or blends as organic solutions or aqueous or organic dispersions by known techniques customarily used in applying fluorochemicals, e.g., fluorochemical acrylate copolymers, to fibers and fibrous substrates. If desired, such known fluorochemicals as fluoroaliphatic radical-containing polymers, e.g., acrylates and methacrylates can be used in conjunction with the above-described fluorochemical allophanate blends. For example, the fluorochemical treatment, with the fluorochemical being in the form of an aqueous emulsion or organic solution, can be carried out by immersing the fibrous substrates in a bath containing the cationic fluorochemical blends, padding the substrate or spraying the same with the fluorochemical emulsions or solutions, or by foam, kiss-roll, or metering applications e.g., spin finishing, and then drying the treated substrates if solvent is present. If desired, the fluorochemical composition or blends can be co-applied with conventional fiber treating agents, e.g., antistatic agents or non-aqueous fiber lubricants.

In the manufacture of synthetic organic fibers (see, for example, the review article in Kirk-Othmer, *Encyclopedia of Polymer Science and Technology*, 8, 374–404, 1968), the first step that normally takes place in the process, following initial formation of the filaments (e.g., by melt spinning or solvent spinning), is coating the fiber surface with a small amount of fiber finish comprising lubricating and antistatic agents. It is particularly advantageous to treat such fibers, e.g., nylon 66 and nylon 6, with the fluorochemical allophanates or blends thereof of this invention in conjunction with the spin finish being applied to such textile fibers.

Fiber finishes are generally produced in the form of dilute aqueous emulsions or as non-aqueous solutions, or dispersions, which principally contains said lubricant and antistatic agents as well as emulsifier (surfactant) and may also contain materials such as bactericides and antioxidants.

Representative lubricants include mineral oils, waxes, vegetable oils (triglycerides) such as coconut oil, peanut oil, and castor oil, synthetic oils, such as esters, polyoxyethylene derivatives of alcohols and acids, and silicone oils.

The antistatic agents, emulsifiers, and surfactants which can be incorporated into the fiber finish are selected from similar chemical classes, which include:
  (a) anionics, such as fatty acid soaps, sulfated vegetable oils, salts of alkyl and ethoxylated alkyl phosphates;
  (b) cationics, such as fatty amines, quaternary ammonium compounds, and quaternary phosphonium compounds;
  (c) nonionics, such as glyceryl monooleate, ethoxylated alcohols, ethoxylated fatty acids, and ethoxylated fatty amides; and
  (d) amphoterics, such as betaines, amino acids and their salts.

A preferred method of applying the fluorochemical allophanate composition blends of this invention to synthetic organic fibers is to incorporate the blend into the above-described fiber finishes in an amount sufficient to achieve the desired properties of oil and water repellency and soil resistance. Generally, the amount of fluorochemical to be used will be that sufficient to retain on the fiber of the finished article, e.g., carpet, about 200 to 1000 ppm fluorine based on the weight of the fiber. Such additions to the conventional fiber finish can be carried out without sacrificing or adversely affecting typical requirements that conventional fiber finishes must meet, namely lubrication, thermal stability, low fuming at elevated temperature, and wetting for fiber dyeability (color addition). The conventional finish components of the fiber finishes containing the fluorochemical allophanates and blends thereof of this invention can be removed in a conventional manner after the fiber is manufactured in fiber form, e.g., carpets and upholstery fabrics. The fluorochemical allophanates and blends thereof withstand the typical conditions encountered during fiber and yarn processing and also survive the more severe processing conditions which the greige goods encounter such as scouring and dyeing, and the finished goods encounter, such as washing, steam cleaning, and dry cleaning. The fluorochemical allophanates and blends thereof do not interfere with, and are durable through, the normal fiber processing steps, e.g., drawing, texturizing, and heat setting, and provide oil and water repellency and anti-soiling properties to the finished article, e.g. carpet made from the treated fibers.

The conventional application methods used to apply finishes to fibers (or filaments) can be used with the fluorochemical allophanates or blends thereof of this invention. Such methods include the use of either (a) a revolving ceramic cylinder, i.e., kiss-roll, which is partially immersed in a pan containing the fluorochemical finish, over which the moving filaments pass and pick up a thin film of finish, (b) a metering pump supplying finish through a slot or hole in a fiber guide over which the moving filaments pass, (c) an immersion finish bath, or (d) spraying devices.

Representative fluorochemical oxyalkylenes useful as component (b) in the fluorochemical blends of this invention are shown in Table 1. Generally, the preparation of the fluorochemical oxyalkylenes results in products which comprise mixtures of oxyalkylenes, the lengths of the fluoroaliphatic radical and the poly(oxyalkylene) moiety varying and the subscripts denoting the number of carbon atoms of the former and denoting the number of oxyalkylene units in a poly(oxyalkylene) segment being in both cases average numbers, and in this specification, e.g., Table 1, those subscripts should be understood as having such average values, unless otherwise indicated.

TABLE 1

| | |
|---|---|
| 1. | $C_8F_{17}SO_2N(C_2H_5)CH_2CO_2(C_2H_4O)_{15}H$ |
| 2. | $C_8F_{17}SO_2N(C_2H_5)C_2H_4O(C_2H_4O)_{14}H$ |
| 3. | $C_8F_{17}C_2H_4O(C_2H_4O)_{15}H$ |
| 4. | $C_8F_{17}SO_2N\begin{matrix}(C_2H_4O)_rH \\ (C_2H_4O)_{r'}H\end{matrix}$    $(r + r' = 25)$ |
| 5. | $C_8F_{17}SO_2N(C_2H_5)C_2H_4O(C_3H_6O)_8H$ |
| 6. | $C_8F_{17}C_2H_4SCHCO_2(C_3H_6O)_rH$    $(r + r' = 20)$ <br> $\quad\quad\quad\quad\;\; \vert$ <br> $\quad\quad\quad\;\; CH_2CO_2(C_3H_6O)_{r'}H$ |
| 7. | $C_8F_{17}SO_2N(C_2H_5)C_2H_4O(C_2H_4O)_{7.5}H$ |

Representative fluorochemical oxyalkylene polyacrylates useful as component (b) in the blends of this invention are those made by copolymerizing any of the fluorochemical acrylates of Table 2 with any of the fluorine-free poly(oxyalkylene)monomers of Table 3.

TABLE 2

1. $C_8F_{17}SO_2N(CH_3)CH_2CH_2OCOCH=CH_2$
2. $C_6F_{13}C_2H_4OCOC(CH_3)=CH_2$
3. $C_6F_{13}C_2H_4SC_2H_4OCOCH=CH_2$
4. $C_8F_{17}C_2H_4OCOC(CH_3)=CH_2$
5. $C_8F_{17}C_2H_4N(CH_3)C_2H_4OCOC(CH_3)=CH_2$
6. $C_2F_5C_6F_{10}CH_2OCOCH=CH_2$
7. $C_7F_{15}CH_2OCOCH=CH_2$
8. $C_7F_{15}CON(CH_3)C_2H_4OCOCH=CH_2$
9. $(CF_3)_2CF(CF_2)_6CH_2CH(OH)CH_2OCOCH=CH_2$
10. $(CF_3)_2CFOC_2F_4C_2H_4OCOCH=CH_2$
11. $C_8F_{17}C_2H_4SO_2N(C_3H_7)C_2H_4OCOCH=CH_2$
12. $C_7F_{15}C_2H_4CONHC_4H_8OCOCH=CH_2$

13. $C_3F_7(CFCF_2O)_2CFCH_2OCOCH=CH_2$
            |        |
            $CF_3$    $CF_3$

14. $C_7F_{15}COOCH_2C(CH_3)_2CH_2OCOC(CH_3)=CH_2$
15. $C_8F_{17}SO_2N(C_2H_5)C_4H_8OCOCH=CH_2$
16. $(C_3F_7)_2C_6H_3SO_2N(CH_3)C_2H_4OCOCH=CH_2$

17. 
$$C_2F_5CF\begin{matrix}CF_2CF_2\\ \diagdown\\ CF_2CF_2\end{matrix}NC_2F_4CON(CH_3)C_2H_4OCOCH=CH_2$$

18. $C_6F_{13}CF=CHCH_2N(CH_3)C_2H_4OCOCH=CH_2$
19. $C_8F_{17}SO_2N(C_4H_9)C_2H_4OCOCH=CH_2$
20. $C_8F_{17}SO_2N(C_2H_5)C_2H_4OCOCH(CH_3)=CH_2$

TABLE 3

1. $CH_2=CHCO_2(C_2H_4O)_{10}(C_3H_6O)_{22}(C_2H_4O)_9C_2H_4OCOCH=CH_2$
2. $CH_2=CHCO_2(C_2H_4O)_{17}CH_3$
3. $CH_2=C(CH_3)CONH(C_3H_6O)_{44}H$
4. $CH_2=C(CH_3)CO_2(C_2H_4O)_{90}COC(CH_3)=CH_2$
5. $HS(C_2H_4O)_{23}(C_3H_6O)_{35}(C_2H_4O)_{22}C_2H_4SH$

Representative compounds of this invention were prepared from the reactants listed in Table 4, following the procedures set forth in Examples 1, 2, and 3 with the structures summarized in Tables 5 and 6, respectively.

TABLE 4

| Code | Reactant Formulas & Codes |
|---|---|
| | Alcohols |
| A1 | $C_8F_{17}SO_2N(C_2H_5)CH_2CH_2OH$ |
| A2 | $C_8F_{17}CH_2CH_2OH$ |
| A3 | $C_8H_{17}OH$ |
| A4 | $N(CH_2CH_2OH)_3$ |
| | Isocyanates |
| IPDI | 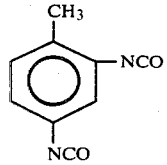 |
| HDI | $OCN(CH_2)_6NCO$ |
| | Isocyanates |
| MDI |  |

TABLE 4-continued

| Code | Reactant Formulas & Codes |
|---|---|
| TDI | (structure: toluene with CH₃, two NCO groups) |
| | Polyols and polyamines |
| C1 | $CH_3CH_2C(CH_2OH)_3$ |
| C2 | $H_2N(CH_2)_6NH_2$ |
| C3 | $HOCH_2CH(OH)C_4H_8OH$ |
| C4 | $HOCH_2CH(OH)CH_2OH$ |
| C5 | $ClCH_2CH(OH)CH_2OH$ |
| C6 | $CH_3C(CH_2OH)_2COOH$ |
| | Catalyst |
| D1 | $Sn(OCOC_7H_{15})_2$ |
| D2 | $(C_4H_9)_2Sn(OCOC_{11}H_{23})_2$ |
| D3 | $(C_2H_5)_3N$ |
| D4 | $(HOC_2H_4)_3N$ |
| | Quaternizing agent or amine |
| E1 | $(C_2H_5)_2SO_4$ |
| E2 | (morpholine: O and NH in ring) |

EXAMPLE 1

In a 3-necked flask fitted with a mechanical stirrer, condenser, gas inlet tube, thermometer, addition funnel and electric heating mantle was place 100.8 g (0.60 moles) of 1,6-hexane diisocyanate (HDI), 100 g of ethyl acetate, 4 drops of stannous octoate and 4 drops of dibutyltindilaurate. The mixture was heated to 80° C. and stirred under an atmosphere of $N_2$ while adding a solution of 332.4 g (0.60 moles) of N-ethyl(perfluorooctane)sulfonamidoethyl alcohol in 200 g of ethyl acetate over a period of 4 hours. Heating at 80° C. was continued for an additional 5 hours until essentially all of the hydroxyl groups had been converted to urethane groups as indicated by IR absorption analysis.

After allowing the reaction mixture to stand at room temperature overnight, the ethyl acetate from the resulting solution was removed under reduced pressure while raising the temperature from 80° C. to 160° C. The temperature was maintained at 160° C. for 4 hours with stirring as the NCO equivalent weight, increased from 848 to 2934 (determined by standard titration procedures). The resulting viscous product was diluted with 380 g of ethyl acetate. To one-half of this solution was added 2.8 g (0.03 moles) glycerol and this mixture was stirred and heated at 75°–80° C. for 4 hours and left at room temperature for 60 hrs. Infrared absorption analysis indicated that all of the remaining isocyanate groups had been converted to urethane groups to yield the fluorochemical allophanate of composition "e" in Table 6, as the principal product.

The above urethane allophanate solution (381 g) was combined with 162 g of additional ethyl acetate and 30 g of "triton" X-102 non-ionic surfactant and warmed to 40° C. To this was added a warmed (40° C.) solution of 4.0 g of fluorochemical surfactant $C_8F_{17}SO_2NH(CH_2)_3N(CH_3)_3Cl$ in 800 g of water and stirred rapidly for 15 minutes at 40° C., then subjected to two passes through a high shear homogenizer. The resulting emulsion was stripped of ethyl acetate (to less than 1% as measured by gas chromatography analysis) by distillation under water aspirator vacuum while heating at 35°–55° C. to yield an aqueous emulsion with 19.6% total solids. The reactants and conditions set forth above are summarized in Table 5. The composition formed is also set forth in Table 6.

EXAMPLE 2

In a 3-necked flask fitted with a mechanical stirrer, condenser, gas inlet tube, thermometer, addition funnel and electric heating mantle was placed 250.0 g (1.0 mole) of methylenebis(4-phenyleneisocyanate), 250 g of ethyl acetate and 8 drops of dibutyltindilaurate. The mixture was heated to 75° C. and stirred under an atmosphere of $N_2$ while adding a solution of 577.0 g (1.0 mole) of N-ethyl(perfluorooctane)sulfonamidoethyl alcohol in 150 g of ethyl acetate over a period of 2.5 hours. The temperature was raised to 80° C. and heating was continued for an additional 4 hours until essentially all of the hydroxyl groups had been converted to urethane groups as indicated by IR absorption analysis.

After allowing the reaction mixture to stand at room temperature for 2½ days, the ethyl acetate from the resulting solution was removed under reduced pressure at 90° C. The temperature was raised to 130°–135° C. and maintained for 9 hours with stirring resulting in an increase in the NCO equivalent weight from 804 to 1,142. The resulting viscous isocyanate-containing allophanate intermediate product was diluted with 800 g of ethyl acetate.

To 25% of the isocyanate-containing allophanate intermediate solution obtained above was added 5.0 g (0.037 mole) of 2,2-dimethylolpropionic acid and the resulting mixture was refluxed for 18 hours while stirring under an atmosphere of $N_2$. IR absorption analysis indicated the presence of isocyanate groups. Glycerol (3.0 g, 0.033 mole) was then added to the reaction mixture and after heating at 65° C. for 4 hours, IR absorption analysis indicated the absence of NCO groups. The resulting amber solution was treated with 3.22 g (0.037 mole) morpholine and heated at 65° C. for 3 hours to yield a mixture of fluorochemical urethane allophanates of composition "b" and "e" in Table 6, as the principal products, "b" being in the form of the morpholine salt.

Following the emulsification procedure of Example 1, the above mixed allophanate product was emulsified. "Tergitol" 15-S-30 was used in place of "Triton" X-120 as the non-ionic surfactant and no quaternary ammonium fluorochemical surfactant was used. The reactants and conditions set forth above are summarized in Table 5, together with the fluorochemical allophanate compositions formed.

EXAMPLE 3

To 25% of the isocyanate-containing allophanate intermediate solution obtained in Example 2 was added 5.0 g (0.0335 mole) of triethanolamine and the resulting mixture was heated at 65° C. for 18 hours while stirring under an atmosphere of $N_2$. IR absorption analysis indicated the presence of isocyanate groups. Glycerol (3.0 g, 0.033 mole) was then added to the reaction mixture and after heating at 65° C. for 4 hours, IR absorption analysis indicated the absence of NCO groups. The resulting solution was treated with 4.9 g (0.032 mole) of diethyl sulfate and heated at 65° C. for 5 hours to yield a mixture of fluorochemical urethane allophanates of composition "e" and "g" in Table 6, as the principal products, "g" being in the form of the quaternary ammonium salt derived from diethyl sulfate.

Following the emulsification procedure of Example 1, the above product was emulsified. A thirty percent solution of a fluorochemical poly(oxyalkylene), a copolymer of $C_8F_{17}SO_2N(CH_3)C_2H_4OCOCH=CH_2$, $CH_2=C(CH_3)COO(CH_2CH_2O)_{90}H$ and $CH=C(CH_3)COO(CH_2CH_2O)_{90}COC(CH_3)=CH_2$, was used in place of "Triton" X-120 as the non-ionic surfactant and no additional quaternary ammonium fluorochemical surfactant was used. The reactants and conditions set forth above are summarized in Table 5, together with the fluorochemical allophanate compositions formed.

EXAMPLES 4–12

Following the general procedures of Examples 1–3, and using the reactants shown in Tables 4 and 5, fluorochemical allophanate compositions and emulsions of this invention were prepared. A summary of reactants, product compositions, and general structures of these preparations are indicated in Tables 5 and 6.

TABLE 5

| Ex. No. | Fluorochemical allophanate composition | Fluorochemical alcohol | Isocyanate | Alcohols polyols, or polyamines | Catalyst | Allophanate-forming temperature, °C. | Equivalent weight* | Quarternizing agent or amine |
|---|---|---|---|---|---|---|---|---|
| 1 | e | A1 | HDI | C4 | D1, D2 | 160 | 3000 | — |
| 2 | b, e | A1 | MDI | C4, C6 | D2 | 135 | 1140 | E2 |
| 3 | e, g | A1 | MDI | C4, A4 | D2 | 135 | 1140 | E1 |
| 4 | c | A1 | IPDI | C2 | D1, D2 | 160 | — | — |
| 5 | d | A1 | IPDI | C3 | D1, D2 | 160 | — | — |
| 6 | e, g | A1 | HDI | C4, A4 | D4 | 165 | 5400 | — |
| 7 | a, g | A1 | IPDI | A4, C1 | D4 | 165 | 900 | — |
| 8 | e | A1 | MDI | C4 | D2 | 135 | 1140 | — |
| 9 | e | A2 | TDI | C4, A3 | D3 | 90 | — | — |
| 10 | e, f | A1 | MDI | C4, C5 | D2 | 135 | 1140 | — |
| 11 | e | A1 | TDI | C4 | D3 | 85 | 1350 | — |
| 12 | h | A1 | TDI | C4, C6 | D3 | 85 | 1300 | E2 |

*Equivalent weight of allophanate/isocyanate intermediate by NCO-group determination

TABLE 6

| a. | $C_2H_5C(CH_2OCONH-Z)_3$ |
|---|---|

TABLE 6-continued

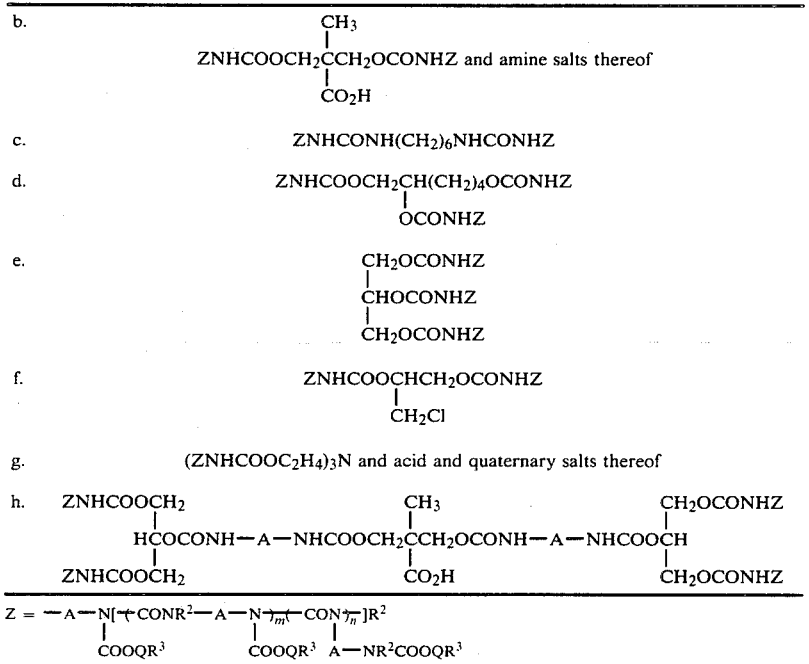

b. 
$$ZNHCOOCH_2\underset{\underset{CO_2H}{|}}{\overset{\overset{CH_3}{|}}{C}}CH_2OCONHZ \text{ and amine salts thereof}$$

c. $ZNHCONH(CH_2)_6NHCONHZ$ d. 
$$ZNHCOOCH_2\underset{\underset{OCONHZ}{|}}{CH}(CH_2)_4OCONHZ$$

e. 
$$\begin{array}{c} CH_2OCONHZ \\ | \\ CHOCONHZ \\ | \\ CH_2OCONHZ \end{array}$$

f. 
$$ZNHCOOCHCH_2OCONHZ \\ \underset{CH_2Cl}{|}$$

g. $(ZNHCOOC_2H_4)_3N$ and acid and quaternary salts thereof h. 
$$\underset{\underset{ZNHCOOCH_2}{|}}{ZNHCOOCH_2}\underset{HCOCONH-A-NHCOOCH_2}{\quad}\underset{\underset{CO_2H}{|}}{\overset{\overset{CH_3}{|}}{C}}CH_2OCONH-A-NHCOOCH\underset{CH_2OCONHZ}{|}$$

$$Z = -A-N[(CONR^2-A-N)_m(CON)_n]R^2 \\ \underset{COOQR^3}{|} \quad \underset{COOQR^3}{|} \quad \underset{A-NR^2COOQR^3}{|}$$

EXAMPLES 13-23

In these examples, several of the fluorochemical allophanates of this invention, specified in Table 7, were used in the form of aqueous emulsions, in the presence of a nonionic textile fiber lubricant and in combination with one or more nonionic surfactants, to treat samples of scoured nylon 66 greige carpet (28 oz/yd²) in a padding application (71% wet puckup).

The fluorochemical treated carpet samples were placed on a paper blotter to remove excess emulsion, then dried in a circulating air oven (25 minutes at 70° C. and 5 minutes at 150° C.).

The fluorochemical treated, dried samples were then acid dyed, excess aqueous dye solution removed, samples rinsed and dried at 70° C. and then heated for 5 minutes at 130° C.

The fluorochemical treated carpet samples were analyzed for fluorine before and after dyeing to measure retention of fluorochemical on the carpet fibers. The fluorochemical treated, dyed samples were evaluated for oil repellency (OR), water repellency (WR) and walk-on soil resistance (WOS). The results are summarized in Table 7.

The water repellency of treated samples is measured using a water/isopropyl alcohol test, and is expressed in terms of a water repellency rating on a scale of 0 to 10 of the treated carpet or fabric. Treated carpets which are penetrated by or resistant only to a 100 percent water/0 percent isopropyl alcohol mixture (the least penetrating of the test mixtures) are given a rating of 0, whereas treated fabrics resistant to a 0 percent water/100 percent isopropyl alcohol mixture (the most penetrating of the test mixtures) are given a rating of 10. Other intermediate values are determined by use of other water/isopropyl alcohol mixtures, in which the percentage amounts of water and isopropyl alcohol are each multiples of 10. The water repellency rating corresponds to the most penetrating mixture which does not penetrate or wet the fabric after 10 seconds contact. In general, a water repellency rating of at least 1 or 2, is desirable for carpet.

The oil repellency of treated carpet and textile samples is measured by AATCC Standard Test 188-1978, which test is based on the resistance of treated fabric to penetration by oils of varying surface tensions. Treated fabrics resistant only to "Nujol", a brand of mineral oil and the least penetrating of the test oils, are given a rating of 1, whereas treated fabrics resistant to heptane (the most penetrating of the test oils) are given a value of 8. Other intermediate values are determined by use of other pure oils or mixtures of oils. The rated oil repellency corresponds to the most penetrating oil (or mixture of oils) which does not penetrate or wet the fabric after 10 seconds contact rather than the 30 seconds contact of the Standard Test. Higher numbers indicate better oil repellency. Additionally, a value of 0 indicates no resistance to "Nujol". In general, an oil repellency of 2 or greater is desirable for carpet.

The soil resistance of treated and untreated (control) carpet was determined by exposure to pedestrian traffic according to AATCC Test method 122-1979, the exposure site being a heavily travelled industrial area for an exposure of about 15,000 "traffics". The samples are repositioned periodically to insure uniform exposure and are vacuumed every 24 hours during the test and before visual evaluation. The evaluation employed the following "Walk-On-Soiling" (WOS) rating system:

| WOS Rating | Description |
|---|---|
| 0 | equal to control |
| ±½ | slightly better (+) or worse (−) than control |
| ±1 | impressive difference compared to control |
| ±1½ | very impressive difference compared to control |
| ±2 | extremely impressive difference compared to control |

Intermediate values are provided where test results were intermediate the WOS rating of AATOC test method 122-1979.

In the tables which follow, the surfactant used is identified according to the following code:

| Code | Surfactant |
|---|---|
| A | poly(oxyalkylene) copolymer of $C_8F_{17}SO_2N(CH_3)C_2H_4OCOCH=CH_2$, $CH_2=C(CH_3)COO(CH_2CH_2O)_{90}H$, and $CH_2=C(CH_3)COO(CH_2CH_2O)_{90}COC(CH_3)=CH_2$ |
| B | "Triton" X-102 |
| C | $C_8F_{17}SO_2NHC_3H_6N(CH_3)_3Cl$ |
| D | "Tween" 80 |
| E | "Tergitol" 15-S-30 |
| F | "Ethoquad" 18/25 |

TABLE 7

| | Fluorochemical compositions | | | Properties of carpet | | | |
|---|---|---|---|---|---|---|---|
| | Fluorochemical Identity | Aqueous emulsion | | Percent fluorochemical | | | |
| Ex. No. | Table 5 No. | Surfactant Code | %* | Total solids | retention through dyeing | Or | WR | WOS |

| Ex. No. | Table 5 No. | Code | %* | Total solids | through dyeing | Or | WR | WOS |
|---|---|---|---|---|---|---|---|---|
| 13 | 1 | B,C | 15,2 | 19.6 | 81 | 4 | 4 | +1¼ |
| 14 | 2 | E | 15 | 22 | 91 | 3 | 6 | +1½ |
| 15 | 3 | A | 30 | 22 | 90 | 5 | 6 | +1½ |
| 16 | 4 | B | 15,2 | 21 | 100 | 4 | 3 | +1¾ |
| 17 | 5 | B,C | 15,2 | 22 | 82 | 4 | 3 | +1½ |
| 18 | 6 | A,C | 35,2 | 24 | 100 | 4 | 8 | +1½ |
| 19 | 7 | A,C | 35,2 | 20 | 69 | 4 | 3 | +1¼ |
| 20 | 8 | A,C,D | 25,2.5, 6.2 | 23 | 63 | 4 | 8 | +1½ |
| 21 | 10 | A,C | 20,2 | 20 | 73 | 5 | 7 | +1¾ |
| 22 | 11 | E | 15 | 23.3 | 60 | 2 | 2 | +1¼ |
| 23 | 12 | E | 15 | 21.7 | 100 | 0 | 2 | +1 |
| Control | — | — | — | 0 | — | 0 | NWR | 0 |

*Percent with respect to fluorochemical allophanate
**NWR means no water-repellency

TABLE 8

| | Surfactant used with fluorochemical | | Percent fluorochemical retention | Properties of carpet | | |
|---|---|---|---|---|---|---|
| Ex. No. | Code | % | through dyeing | OR | WR | WOS |
| 24 | D,F | 15,2 | 83 | 3 | 3 | +½ |
| 25 | — | — | — | 0 | NWR | 0 |

The test data show that the fluorochemical allophanate provided the carpet with good oil and water repellency and useful soil resistance and was retained on the fiber through the drawing, texturing, tufting and dyeing processes.

The test data show that nylon carpet pad-treated with the fluorochemical allophanate has good oil and water repellency and soil resistance and that the fluorochemical allophanate is retained on the carpet through the dyeing process.

EXAMPLES 24–25

Example 24 describes the treatment of nylon carpet fiber with 0.2% (based on %F) aqueous emulsions of a fluorochemical allophanate of composition No. 4 of Table 5, in combination with a 3.5 wt. % aqueous emulsion of a coconut oil-based fiber spin finish, and a fluorochemical oxyalkylene and hydrocarbon nonionic surfactant, as indicated in Table 8.

The fluorochemical spin finish emulsion composition adjusted to 0.2% fluorochemical (based on F content) was applied by a metered slot applicator to melt extruded, undrawn yarn of nylon 66. The yarn was made of 100 filaments of 20 denier (per filament). The treated yarn was continuously drawn and texturized and made into level-loop carpet (28 oz/yd²), heat set at 190° C. for one minute, acid dyed, dried at 70° C. for 30 min., heated at 130° C. for 10 min., and then evaluated, together with an untreated control, Example 25, for oil and water repellency, walk-on soil resistance, and retention of fluorochemical through the dyeing process as determined by fluorine analysis. The test results are shown in Table 8.

EXAMPLES 26–31

In Examples 26 and 27, two different rainwear fabrics were treated with an aqueous emulsion of a fluorochemical allophanate of Example No. 3 of Table 5, in combination with a fluorochemical oxyalkylene surfactant, as indicated in Table 9. In Examples 28 and 29, two different rainwear fabrics were treated with an aqueous emulsion of 65 wt. percent of a copolymer of the fluorochemical acrylate No. 1 of Table 2 and butyl acrylate, 95 wt. percent and 5 wt. percent respectively, and 35 wt. percent of the fluorochemical allophanate of Example 2 in combination with the surfactants indicated in Table 9. The fabrics were treated in a padding operation, dried at 150° C. for 10 min., and evaluated, together with untreated fabrics, Examples 30 and 31, for initial oil repellency (OR) and resistance to a water spray (SR), then these properties evaluated again after 5 launderings (5L) and also after one dry cleaning (DC).

The OR test used was the above-described AATCC Standard Test 118-1978, the contact time before observation being the specified 30 sec., an OR value of 3 or greater being particularly desirable for rainwear fabrics.

The water spray rating (SR) is measured by AATCC Test Method 22-1979. The spray rating is measured using a 0 to 100 scale where 100 is the highest possible rating. In general, a spray rating of 70 or greater is desirable, particularly for outerwear fabrics.

The treated fabrics were laundered using a mechanically agitated automatic washing machine capable of containing a 4 kg load, using water at 50° C. and a commercial detergent, and then the washed fabrics were tumble-dried in an automatic dryer for 40 minutes at 70° C. and pressed in a flat-bed press (at 154° C.) before testing.

The treated fabrics were dry cleaned using perchloroethylene containing 1% of a dry cleaning detergent and tumbling in a motor driven tumble jar (AATCC Test Method 70-1975) for 20 minutes at 25° C. After removing excess solvent in a wringer, samples were dried at 70° C. for 10 minutes, then pressed on each side for 15 seconds on a flat-bed press maintained at 154° C.

The test data are summarized in Table 9.

TABLE 9

| Ex. No. | Surfactant used with fluorochemical | | Properties of fabric | | | | | |
|---|---|---|---|---|---|---|---|---|
| | Code | % | % SOF$^a$ | Fabric$^b$ | Initial | | 5L | | DC | |
| | | | | | OR | SR | OR | SR | OR | SR |
| 26 | A | 30 | 0.2 | A | 6 | 70 | 5 | 70 | 5 | 70 |
| 27 | A | 30 | 0.2 | B | 6 | 70 | 5 | 70 | 6 | 70 |
| 28 | E | 15 | 0.1 | C | 5 | 100 | 2 | 100 | 4 | 80 |
| | F | 5 | | | | | | | | |
| 29 | E | 15 | 0.1 | A | 6 | 100 | 5 | 100 | 5 | 80 |
| | F | 5 | | | | | | | | |
| 30 | — | — | 0 | A | 0 | 0 | 0 | 0 | 0 | 0 |
| 31 | — | — | 0 | B | 0 | 0 | 0 | 0 | 0 | 0 |

$^a$Percent fluorochemical solids on fabric
$^b$Fabric A is 100% woven polyester; fabric B is 100% nylon taffeta; fabric C is woven 65/55 polyester/cotton blend.

The test data show that the rainwear fabrics were provided with oil and water repellency by the fluorochemical allophanate, with retention of repellency through laundering and dry cleaning.

EXAMPLES 32–34

In Examples 32–34, water-leaf paper sheets were treated with an aqueous emulsion of a fluorochemical allophanate of Example No. 3 of Table 5, in combination with a fluorochemical oxyalkylene and hydrocarbon nonionic surfactant, as indicated in Table 10.

The paper sheets were treated with various concentration of the fluorochemical emulsion compositions using a laboratory size press (yielding a 93% wet pickup) and the sheets dried in a photo sheet dryer at 150° C. and evaluated for oil and water repellency. A comparative untreated paper sheet was also evaluated for oil and water repellancy. The results are given in Table 10.

TABLE 10

| Ex. No. | Surfactant used with fluorochemical | | Concentration of fluorochemical in bath, wt. % | Amount of fluorochemical on paper, wt. % | Oil repellency$^a$ | Water repellency$^b$ |
|---|---|---|---|---|---|---|
| | Code | % | | | | |
| 32 | A | 30 | 1.47 | 0.3 | 8 | 230 |
| 33 | A | 30 | 2.44 | 0.5 | 9 | 210 |
| 34 | A | 30 | 4.88 | 1.0 | 10+ | 210 |
| Control | — | — | — | — | 0 | NWR |

$^a$This was determined by the "Kit Test" described as TAPPI Useful Method 557; the higher the value the better the repellency.
$^b$This was determined by the "Cobb Test" described as TAPPI-T441-OS-77; the lower the value, the better the water repellency.

The test results show that the paper was provided with oil and water repellency by the application of the fluorochemical allophanate, with levels of repellency increasing with increased fluorochemical allophanate application.

EXAMPLE 35

In this example, a rayon/cotton velvet, 100% rayon face, 100% cotton back, upholstery fabric was treated with an aqueous emulsion of a fluorochemical allophanate of Example No. 3 of Table 5, in combination with a fluorochemical oxalkylene surfactant as indicated in Table 11.

The fabric was treated in a padding operation, dried at 150° C. for 10 min., and evaluated together with an untreated control fabric for initial oil repellency (OR) and resistance to a water spray (SR) using the test procedures described above. The oil repellency of the tested fabric after abrasion is measured by abrading 5 cm × 12.5 cm samples of fabric (the long dimension is the warp direction) using 40 back-and-forth rubs over a 20 second period with No. 600 abrasive paper ("WE-TORDRY TRI-M-ITE", commercially available from 3M Co.) in an AATCC crockmeter. The above described AATCC oil repellency Test 118-1978 is performed on the abraded sample and the oil repellency rating recorded. In general, an oil repellency after abrasion of 3 or greater is desirable.

The test data are summarized in Table 11.

TABLE 11

| Example No. | Surfactant used with fluorochemical | | Properties of fabric | | | |
|---|---|---|---|---|---|---|
| | Code | % | % SOF | Initial OR | Abraded OR | SR |
| 35 | A | 30 | 0.3 | 4 | 4 | 70 |
| Control | None | — | 0 | 0 | 0 | 0 |

EXAMPLES 36–37

In these examples, upholstery fabrics were treated in a padding operation with a 0.39 weight percent solution of fluorochemical allophanate of Example No. 9 of Table 5 in isopropyl alcohol. (No surfactants were used). The drying and test procedures used were the same as for Examples 37 and 38. The test data are summarized in Table 12.

TABLE 12

| Example No. | % SOF | Fabric$^a$ | Initial OR | Abraded OR | SR |
|---|---|---|---|---|---|
| 36 | 0.3 | D | 3 | 3 | 70 |

TABLE 12-continued

| Example No. | % SOF | Fabric[a] | Initial OR | Abraded OR | SR |
|---|---|---|---|---|---|
| 37 | 0.3 | E | 2 | 1 | 70 |
| Control | 0 | D | 0 | 0 | 0 |
| Control | 0 | E | 0 | 0 | 0 |

[a]Fabric D is a rayon/cotton velvet, 100% rayon face, 100% cotton back; fabric E is rayon/cotton velvet, 79/21 rayon/cotton face and 36/64 rayon/cotton back.

EXAMPLES 38-39

In Example 38, a gold-colored, plush, cut-pile, pre-wet nylon carpet (50 oz/yd$^2$) was treated by top spray application (15% wet pickup) of a diluted mixture of an aqueous emulsion of the fluorochemical allophanate composition of Example 3 of Table 5 and an aqueous emulsion of a fluorochemical oxyalkylene surfactant, the dilution (with water) of the mixture of emulsions being done to obtain the desired concentration of fluorochemical necessary to deposit the amount (SOF) of fluorochemical on the carpet speciifed in Table 13. The treated carpet sample was dried for 30 minutes at 70° C. and heated further at 130° C. for 10 min. and then evaluated for OR, WR and WOS. Comparative Example 39 was not treated with fluorochemicals. The results are summarized in Table 13.

TABLE 13

| | Surfactant used with fluorochemical | | Properties of fabric | | |
|---|---|---|---|---|---|
| Ex. No. | Code | % | % SOF[a] | OR | WR | WOS |
| 38 | A | 30 | 0.2 | 0 | 2 | +1¼ |
| 39 | — | — | — | 0 | 0 | 0 |

[a]% fluorochemical solids on fabric.

As can be seen from the results in Table 13, water repellancy and soil resistance were attained, although oil repellency was not attained.

Various modifications and alterations of this invention will be apparent to those skilled in the art without departing from the scope and spirit of this invention and this invention should not be restricted to that set forth herein for illustrative purposes.

What is claimed is:

1. Fluorochemical allophanates comprising one or more monovalent fluoroaliphatic radicals having at least three fully fluorinated terminal carbon atoms and one or more allophanate moieties, said radicals and moieties bonded together by first organic linking groups, which may contain hetero atoms, said first linking groups being free of groups with active hydrogen atoms, and where said fluorochemical allophanates contain amino or acid moieties, one or more linked fluoroaliphatic radicals and allophanate moieties are present, and where said fluorochemical allophanates are free of amino and acid moieties, two or more of said linked fluoroaliphatic radicals and allophanate moieties are bonded together by polyvalent second organic linking groups, which may contain hetero atoms; said second linking groups being free of groups with active hydrogen atoms.

2. Fluorochemical allophanates according to claim 1, wherein said fluorochemical allophanates are represented by the general formula

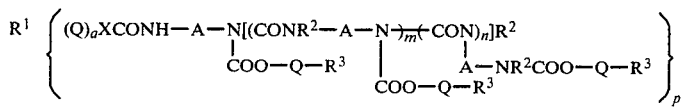

where $R^1$ is an organic radical; $R^2$ is selected from H or CONH-A-NHCOOQR$^3$; $R^3$ is a terminal monovalent organic radical; A is an organic linking group, which may contain hetero atoms; Q is an organic linking group, which may contain hetero atoms; X is O, S or NR$^4$, where R$^4$ is H or lower alkyl having 1 to 4 carbon atoms; at least one R$^3$ or A contains said perfluoroaliphatic radical (R$_f$); a is a number from 0 to 1; m and n are independently numbers from 0 to 10, the sum of m and n is 1 to 10, and each of the moieties denoted by subscripts m and n, when both are present, are randomly distributed in a chain within the brackets, [ ]; p is a number from 2 to 6.

3. Fluorochemical allophanates according to claim 2 where $R^1$ is selected from

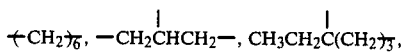

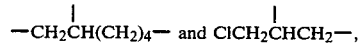

$R^3$ is $C_nF_{2n+1}$ where n is an integer of from 6 to 12, A is selected from —CH$_2$—$_6$, —C$_6$H$_4$CH$_2$C$_6$H$_4$—,

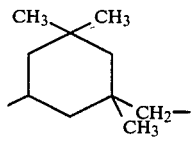

and —C$_6$H$_3$(CH$_3$)—, X is selected from O and NH, Q is selected from —CH$_2$—$_e$ and —SO$_2$NR$^4$CH$_2$—$_e$ where e is 1 to 6 and R$^4$ is an alkyl group having 1 to 4 carbon atoms, and a is 0.

4. Fluorochemical allophanates according to claim 3 where $R^1$ is

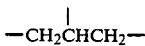

or ${+}$CH$_2{+}_6$, R$_3$ is C$_8$F$_{17}$, Q is —SO$_2$N(C$_2$H$_5$)C$_2$H$_4$— and A is ${+}$CH$_2{+}_6$ or —C$_6$H$_4$CH$_2$C$_6$H$_4$—.

5. Fluorochemical allophanates according to claim 4 where A is —C$_6$H$_4$CH$_2$C$_6$H$_4$— and R$^1$ is

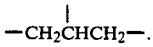

6. Fluorochemical allophanates according to claim 1, wherein said fluorochemical allophanates are represented by the general formula

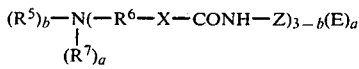

where Z is

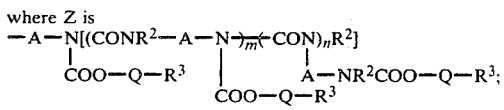

$R^2$ is selected from H or COHN-A-NHCOOQR$^3$; R$^3$ is a terminal monovalent organic radical; A is an organic linking group, which may contain a hetero atom; Q is an organic linking group, which may contain a hetero atom; X is O, S, NR$^4$, where R$^4$ is H or lower alkyl having 1 to 4 carbon atoms; at least one R$^3$ or A contains said fluoroaliphatic radical (R$_f$); R$^5$ is a monovalent radical selected from H, alkyl, aryl, and cycloaliphatic groups; R$^6$ is a divalent organic radical; R$^7$ is selected from H, lower alkyl groups having 1 to 4 carbon atoms, and aralkyl groups having 7 to 13 carbon atoms; E is an anion derived from a protonic acid or an alkylating agent; a is a number from 0 to 1; be is a number from 0 to 2; m and n are independently numbers from 0 to 10, the sum of m and n is 1 to 10, and each of the moieties denoted by subscripts m and n, when both are present, are randomly distributed in a chain within brackets, [ ].

7. Fluorochemical allophanates according to claim 6 where R$^6$ is —CH$_2$CH$_2$—, R$^7$ is a lower alkyl group having 1 to 4 carbon atoms, and E is an anion derived from a protonic acid selected from hydrochloric acid, formic acid, glycolic acid and acetic acid or an alkylating agent selected from diethyl sulfate and alkyl chloride.

8. Fluorochemical allophanates according to claim 7 where R$^7$ is CH$_3$CH$_2$—, E is CH$_3$CH$_2$SO$_4$—, X is O, a is 1, and b is 0.

9. Fluorochemical allophanates according to claim 1 wherein said fluorochemical allophanates are represented by the general formula (G)$_a$R$^1$[(R$^6$)$_a$(X—CONH—Z)$_c$]$_d$ where Z is

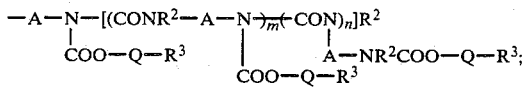

R$^1$ is a polyvalent organic linking group; R$^2$ is selected from H or CONH—A—NHCOOQR$^3$; R$^3$ is a terminal monovalent organic radical; Q is an organic linking group, which may contain hetero atoms; A is an organic linking group, which may contain hetero atoms; X is O, S, or NR$^4$, where R$^4$ is H or lower alkyl having 1 to 4 carbon atoms; at least one R$^3$ or A contains said perfluoroaliphatic radical (R$_f$); G is an anionic group selected from COOM$_{1/v}$, SO$_3$M$_{1/v}$, PO(OM$_{1/v}$)$_2$, OSO$_3$M$_{1/v}$, and OPO(OM$_{1/v}$)$_2$ where M is hydrogen or a cationic moiety and v is a valence of M; a is a number from 0 to 1; m and n are independently numbers from 0 to 10, the sum of m and n is 1 to 10, and each of the moieties denoted by subscripts m and n, when both are present, are randomly distributed with brackets, [ ]; c is 1 to 2; and d is a number from 1 to 6, except when a is 0, d is a number from 2 to 6.

10. Fluorochemical allophanates according to claim 9 where G is —COOM$_{1/v}$, R$^6$ is —CH$_2$—, R$^1$ is

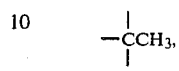

X is O, a is 1, and d is 2.

11. Fluorochemical allophanates according to claim 9 where G is COO—

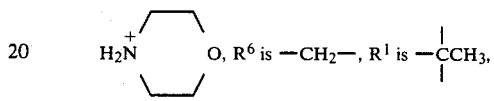

a is 1, c is 1 and d is 2.

12. Fluorochemical allophanates according to claim 1, wherein said fluorochemical allophanates are represented by the general formula

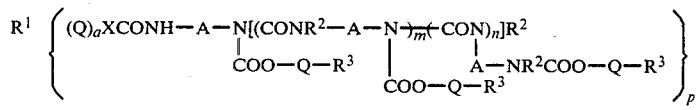

where R$^1$ is an organic radical; R$^2$ is selected from H or CONH—A—NHCOOQR$^3$; R$^3$ is a terminal monovalent organic radical; A is an organic linking group, which may contain hetero atoms; Q is an organic linking group, which may contain hetero atoms; X is O, S or NR$^4$, where R$^4$ is H or lower alkyl having 1 to 4 carbon atoms; at least one R$^3$ or A contains a perfluoroaliphatic radical (R$_f$); at least one R$^1$ or R$^3$ contains an amino or acid moiety; a is a number from 0 to 1; m and n are independently numbers from 0 to 10, the sum of m and n is 1 to 10, and each of the moieties denoted by subscripts m and n, when both are present, are randomly distributed in a chain within the brackets, [ ]; and p is a number from 1 to 6.

13. A fluorochemical composition comprising a blend of the fluorochemical allophanate of claim 1 and a fluoroaliphatic radical-containing poly(oxyalkylene) having one or more monovalent fluoroaliphatic radicals having at least three fully fluorinated carbon atoms and one or more poly(oxyalkylene) moieties, said radicals and moieties bonded together by hetero atom-containing or organic linking groups.

14. A fluorochemical composition comprising a blend of the fluorochemical allophanate of claim 2 or 12 and the fluorochemical allophanate of claim 6.

15. A fluorochemical composition comprising a blend of the fluorochemical allophanate of claim 2 or 12 and the fluorochemical allophanate of claim 9.

16. A fluorochemical composition comprising a blend of the fluorochemical allophanate of claim 1 and a compound selected from fluorochemical urethane, fluorochemical polyacrylates, hydrocarbon polyacrylates, and combinations thereof.

17. Fluorochemical allophanates produced according to a process comprising the steps of
  (a) reacting alcohol containing a fluoroaliphatic radical having at least three fully fluorinated terminal carbon atoms with an organic diisocyanate under urethane forming conditions to form fluorochemical isocyanate-containing urethane adduct,
  (b) heating said adduct under allophanate forming reaction conditions to form a fluorochemical isocyanate-containing allophanate intermediate, and
  (c) reacting said intermediate with a reactant selected from polyol or polyamine under urethane or urea forming reaction conditions to produce fluorochemical allophanate.

18. Fluorochemical allophanates produced according to a process comprising the steps of
  (a) reacting alcohol containing a fluoroaliphatic radical having at least three fully fluorinated terminal carbon atoms with an organic diisocyanate under urethane forming conditions to form fluorochemical isocyanate-containing urethane adduct,
  (b) heating said adduct under allophanate forming reaction conditions to form a fluorochemical isocyanate-containing allophanate intermediate,
  (c) reacting said intermediate with a reactant selected from a polyamine, an alcohol containing an acid moiety, and an alcohol containing an amine moiety under urethane or urea forming reaction conditions to produce an amino- or acid-containing fluorochemical allophanate, and
  (d) neutralizing said amino- or acid-containing fluorochemical allophanate to form fluorochemical allophanate salts.

19. Fluorochemical allophanates produced according to a process comprising the steps of
  (a) reacting alcohol containing a fluoroaliphatic radical having at least three fully fluorinated terminal carbon atoms with an organic diisocyanate under urethane forming conditions to form fluorochemical isocyanate-containing urethane adduct,
  (b) heating said adduct under allophanate forming reaction conditions to form a fluorochemical isocyanate-containing allophanate intermediate,
  (c) reacting said intermediate with a reactant selected from a polyamine or an amino alcohol under urethane or urea forming reaction conditions to produce an amino-containing fluorochemical allophanate, and
  (d) alkylating said amino-containing fluorochemical allophanate to form fluorochemical allophanate salts.

20. A fiber finish comprising an organic solution or aqueous emulsion of the fluorochemical composition of claim 1.

21. A method for imparting oil and water repellency and soil resistance to a fibrous substrate which comprises treating the fibers thereof with the fiber finish of claim 20.

22. An oil and water repellent fibrous substrate coated with the fluorochemical composition of claim 1.

23. A process for rendering a fibrous substrate durably oil and water repellent and soil resistant comprising the steps of contacting the fibers thereof with a liquid composition containing the fluorochemical allophanate of claim 1, and drying said liquid composition on said fibers.

24. A coating formed from the fluorochemical allophanates of claim 1.

25. A coated shaped fibrous article coated with the fluorochemical composition of claim 1.

26. Fluorochemical allophanates comprising (a) one or more monovalent fluoroaliphatic radicals having at least three fully fluorinated terminal carbon atoms (b) one or more allophanate moieties, said radicals and moieties linked or bonded together by first organic linking groups, which may contain hetero atoms, said first linking groups being free of active hydrogen atoms, and (c) organo amino or acid moieties, combinations thereof, with the proviso that when two or more of said linked fluoroaliphatic radicals and allophanate moieties are present, said linked fluoroaliphatic radicals and allophanates moieties are bonded together by polyvalent second organic linking groups, which may contain hetero atoms, said second linking groups being free of active hydrogen atoms.

27. Fluorochemical allophanates comprising one or more monovalent fluoroaliphatic radicals, each having at least three fully fluorinated terminal carbon atoms, and one or more allophanate moieties, said radicals and moieties bonded together by first organic linking groups, which may contain hetero atoms, said first linking groups being free of active hydrogen atoms, and said fluorochemical allophanates having at least two or more of said linked fluoroaliphatic radicals and allophanate moieties bonded together by polyvalent second organic linking groups, which may contain hetero atoms.

28. Fluorochemical allophanates comprising one or more monovalent fluoroaliphatic radicals having at least three fully fluorinated terminal carbon atoms and one or more allophanate moieties, said radicals and moieties linked or bonded together by first organic linking groups, which may contain hetero atoms, said first linking groups being free of groups with active hydrogen atoms and being selected from aliphatic, aromatic, oxy, thio, carbonyl, sulfone, sulfoxy, —N(CH$_3$)—, sulfonamido, carbonamido, sulfonamidoalkylene, carbonamidoalkylene, carbonyloxy, urethane, urylene, and combinations thereof, and said fluorochemical allophanates having at least two or more of said linked fluoroaliphatic radicals and allophanate moieties bonded goether by second organic linking groups, which may contain hetero atoms, said second linking groups being free of groups with active hydrogen atoms.

29. Fluorochemical allophanates comprising (a) one or more monovalent fluoroaliphatic radicals having at least three fully fluorinated terminal carbon atoms (b) one or more allophanate moieties, said radicals and moieties bonded together by first organic linking groups, which may contain hetero atoms, said first linking groups being free of active hydrogen atoms and being selected from aliphatic, aromatic, oxy, thio, carbonyl, sulfone, sulfoxy, —N(CH$_3$)—, sulfonamido, carbonamido, sulfonamidoalkylene, carbonamidoalkylene, carbonyloxy, urethane, urylene, and combinations thereof, and (c) organo amino or acid moieties, combinations thereof, and salts thereof; with the proviso that when two or more of said allophanate moieties are preent, said moieties are bonded together by second organic linking groups, which may contain hetero atoms, said second linking groups being free of active hydrogen atoms.

* * * * *